(12) United States Patent
Palma et al.

(10) Patent No.: US 11,744,535 B2
(45) Date of Patent: Sep. 5, 2023

(54) AUTOMATED POPULATION BASED ASSESSMENT OF CONTRAST ABSORPTION PHASES

(71) Applicant: International Business Machines Corporation, Armonk, NY (US)

(72) Inventors: Giovanni John Jacques Palma, Chaville (FR); Arkadiusz Sitek, Ashland, MA (US)

(73) Assignee: International Business Machines Corporation, Armonk, NY (US)

( * ) Notice: Subject to any disclaimer, the term of this patent is extended or adjusted under 35 U.S.C. 154(b) by 289 days.

(21) Appl. No.: 17/209,749

(22) Filed: Mar. 23, 2021

(65) Prior Publication Data

US 2022/0304641 A1 Sep. 29, 2022

(51) Int. Cl.
*A61B 6/00* (2006.01)
*G06T 5/40* (2006.01)
*G06T 7/00* (2017.01)
*G16H 30/20* (2018.01)
*G16H 30/40* (2018.01)
*G16H 50/20* (2018.01)
(Continued)

(52) U.S. Cl.
CPC ............... *A61B 6/481* (2013.01); *G06T 5/40* (2013.01); *G16H 30/20* (2018.01); *G16H 30/40* (2018.01); *G16H 50/20* (2018.01); *G16H 50/30* (2018.01); *G06T 2207/30104* (2013.01)

(58) Field of Classification Search
None
See application file for complete search history.

(56) References Cited

U.S. PATENT DOCUMENTS 8,428,969 B2 4/2013 Hahn
2005/0228291 A1* 10/2005 Chance ............... A61B 5/0042
600/407
2009/0094058 A1 4/2009 Reiner
(Continued)

OTHER PUBLICATIONS van Sloun et al. "Entropy of Ultrasound-Contrast-Agent Velocity Fields for Angiogenesis Imaging in Prostate Cancer," IEEE Transactions on Medical Imaging, vol. 36, No. 3, Mar. 2017 (Year: 2017).*

(Continued)

*Primary Examiner* — Soo Shin
(74) *Attorney, Agent, or Firm* — Monchai Chuaychoo

(57) ABSTRACT

Disclosed are techniques for automated analysis and assessments of contrast medium absorption phases in contrast medium based medical images. A target image set includes a plurality of medical images acquired to image a plurality of contrast medium absorption phases. For the images of the target image set, a set of contrast medium absorption phase probabilities are determined corresponding to likelihoods that a given image corresponds to a given contrast medium absorption phase. The determined sets of contrast medium absorption phases are compared against a reference set of contrast medium absorption phases to determine differences to determine a set of matching scores indicative of how closely the contrast medium absorption phases of the target image set align with the plurality of contrast medium absorption phases as compared to the reference set of contrast medium absorption phases.

20 Claims, 8 Drawing Sheets

(51) Int. Cl.
*G16H 50/30* (2018.01)
*G16H 50/70* (2018.01)

(56) References Cited

U.S. PATENT DOCUMENTS

| | | | |
|---|---|---|---|
| 2009/0190840 A1* | 7/2009 | Gundel | G06T 7/0012 |
| | | | 382/224 |
| 2011/0002520 A1* | 1/2011 | Suehling | G06T 7/0012 |
| | | | 382/154 |
| 2011/0276346 A1 | 11/2011 | Reiner | |
| 2011/0282194 A1 | 11/2011 | Reiner | |
| 2014/0275945 A1 | 9/2014 | Fonte | |
| 2015/0087957 A1* | 3/2015 | Liu | G06T 7/0016 |
| | | | 600/408 |
| 2018/0144466 A1 | 5/2018 | Hsieh | |
| 2020/0160993 A1 | 5/2020 | Xie | |

OTHER PUBLICATIONS

M. Eberhard et al., "Machine Learning and Deep Neural Networks Applications in Patient and Scan Preparation, Contrast Medium, and Radiation Dose Optimization", Journal of Thoracic Imaging, vol. 35, pp. 1-4, May 2020, <www.thoracicimaging.com>.
R. Hinzpeter et al., "CT Angiography of the Aorta: Contrast Timing by Using a Fixed versus a Patient-specific Trigger Delay", Radiology 2019, pp. 1-8, <https://doi.org/10.1148/radiol.2019182223>.

* cited by examiner

AUTOMATED POPULATION BASED ASSESSMENT OF CONTRAST ABSORPTION PHASES

BACKGROUND

The present invention relates generally to the field of automated medical imaging analysis, and more particularly to automated contrast medium absorption phase assessments of medical imaging modalities.

Medical imaging is defined as techniques and processes of imaging the interior of a body for clinical analysis and medical intervention, as well as visual representation of the function of some organs or tissues (physiology). Medical imaging aims to reveal internal structures hidden by the skin and bones, as well as to diagnose and treat illnesses and diseases. Medical imaging also assists in establishing datasets of normal anatomy and physiology to make it possible to identify abnormalities. Although imaging of removed organs and tissues are sometimes performed for medical reasons, such procedures are typically considered part of pathology instead of medical imaging. As a discipline and in its broadest sense, medical imaging is part of biological imaging and incorporates radiology, which uses the imaging technologies of X-ray radiography, magnetic resonance imaging, ultrasound, endoscopy, elastography, tactile imaging, thermography, medical photography, nuclear medicine functional imaging techniques as positron emission tomography (PET) and single-photon emission computed tomography (SPECT).

Magnetic resonance imaging (MRI) is a specific medical imaging technique used in radiology to generate pictures of the anatomy as well as the physiological processes of the body. MRI scanners use powerful magnetic fields, magnetic field gradients, and radio waves to generate images of the organs in the body. MRI does not rely on X-rays or the use of ionizing radiation, which distinguishes it from computed tomography (CT) and PET scans.

A CT scan or computed tomography scan (formerly known as a computed axial tomography or CAT scan) is a medical imaging technique which uses computer-processed combinations of a plurality of X-ray measurements taken from several different angles to produce tomographic (cross-sectional) images of a body (or virtual "slices"), providing means to see inside of a body without cutting. The personnel that perform CT scans are called radiographers or radiologic technologists.

A contrast medium (or contrast agent) is a substance used to increase the contrast of structures or fluids within the body in medical imaging. Contrast agents absorb or alter external electromagnetism or ultrasound, which is different from radiopharmaceuticals that emit radiation themselves. In x-ray based imaging, contrast media amplify the radiodensity in a target tissue or structure. In MRIs, contrast media shorten (or in some instances increase) the relaxation times of nuclei within body tissues in order to adjust the contrast in the image.

As the term is used in this document, "medical image modalities" are defined as different techniques and/or medical imaging machines for producing various kinds of images of living bodies for medical purposes. Some examples of known medical imaging modalities include the following: Positron emission tomography (PET), Fludeoxyglucose for Glucose metabolism, O-15 as a flow tracer, Single photon emission computed tomography (SPECT), Computed tomography (CT) perfusion imaging, Functional magnetic resonance imaging (fMRI), Diffusion MRI, Perfusion (blood flow), Arterial spin labeling MRI, Hyperpolarized carbon-13 MRI, Functional photoacoustic microscopy (fPAM), Magnetic particle imaging (MPI), Near-infrared spectroscopy (NIRS).

SUMMARY

According to an aspect of the present invention, there is a method, computer program product and/or system that performs the following operations (not necessarily in the following order): (i) receiving a contrast medium based medical image set, including a target image set, where images in the contrast medium medical image set correspond to a plurality of contrast medium absorption phases; (ii) receiving a reference set of contrast medium absorption phase probabilities; (iii) determining, for each image in the target image set, a set of contrast medium absorption phase probabilities; and (iv) computing a set of matching scores between the sets of contrast medium absorption phase probabilities of the target image set and the reference set of contrast medium absorption phase probabilities.

DETAILED DESCRIPTION

Figure 1:
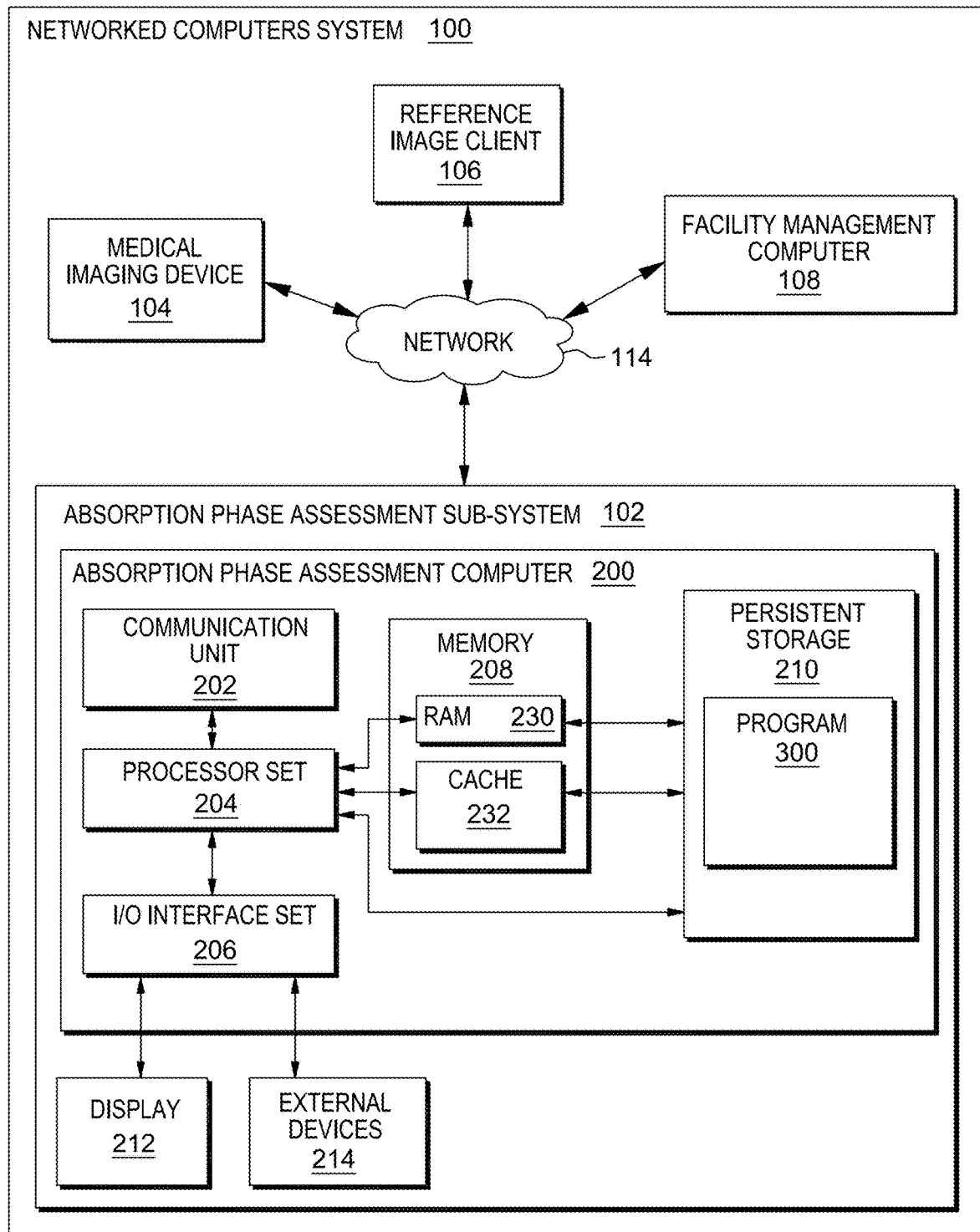
FIG. 1 is a block diagram view of a first embodiment of a system according to the present invention.

Some embodiments of the present invention are directed to techniques for automated analysis and assessments of contrast medium absorption phases in contrast medium based medical images. A target image set includes a plurality of medical images acquired to image a plurality of contrast medium absorption phases. For the images of the target image set, a set of contrast medium absorption phase probabilities are determined corresponding to likelihoods that a given image corresponds to a given contrast medium absorption phase. The determined sets of contrast medium absorption phases are compared against a reference set of contrast medium absorption phases to determine differences to determine a set of matching scores indicative of how closely the contrast medium absorption phases of the target image set align with the plurality of contrast medium absorption phases as compared to the reference set of contrast medium absorption phases.

This Detailed Description section is divided into the following subsections: (i) The Hardware and Software Environment; (ii) Example Embodiment; (iii) Further Comments and/or Embodiments; and (iv) Definitions.

I. The Hardware and Software Environment

The present invention may be a system, a method, and/or a computer program product. The computer program product may include a computer readable storage medium (or media) having computer readable program instructions thereon for causing a processor to carry out aspects of the present invention.

The computer readable storage medium sometimes referred to as a machine readable storage device, can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (for example, light pulses passing through a fiber-optic cable), or electrical signals transmitted through a wire.

A "storage device" is hereby defined to be any thing made or adapted to store computer code in a manner so that the computer code can be accessed by a computer processor. A storage device typically includes a storage medium, which is the material in, or on, which the data of the computer code is stored. A single "storage device" may have: (i) multiple discrete portions that are spaced apart, or distributed (for example, a set of six solid state storage devices respectively located in six laptop computers that collectively store a single computer program); and/or (ii) may use multiple storage media (for example, a set of computer code that is partially stored in as magnetic domains in a computer's non-volatile storage and partially stored in a set of semiconductor switches in the computer's volatile memory). The term "storage medium" should be construed to cover situations where multiple different types of storage media are used.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As shown in FIG. 1, networked computers system 100 is an embodiment of a hardware and software environment for use with various embodiments of the present invention. Networked computers system 100 includes: absorption phase assessment subsystem 102 (sometimes herein referred to, more simply, as subsystem 102); medical imaging device 104; reference image client 106; facility management computer 108; and communication network 114. Absorption phase assessment subsystem 102 includes: absorption phase assessment subsystem computer 200; communication unit 202; processor set 204; input/output (I/O) interface set 206; memory 208; persistent storage 210; display 212; external device(s) 214; random access memory (RAM) 230; cache 232; and program 300.

Subsystem 102 may be a laptop computer, tablet computer, netbook computer, personal computer (PC), a desktop computer, a personal digital assistant (PDA), a smart phone, or any other type of computer (see definition of "computer" in Definitions section, below). Program 300 is a collection of machine readable instructions and/or data that is used to create, manage and control certain software functions that will be discussed in detail, below, in the Example Embodiment subsection of this Detailed Description section.

Subsystem 102 is capable of communicating with other computer subsystems via communication network 114. Network 114 can be, for example, a local area network (LAN), a wide area network (WAN) such as the Internet, or a combination of the two, and can include wired, wireless, or fiber optic connections. In general, network 114 can be any combination of connections and protocols that will support communications between server and client subsystems.

Subsystem 102 is shown as a block diagram with many double arrows. These double arrows (no separate reference numerals) represent a communications fabric, which provides communications between various components of subsystem 102. This communications fabric can be implemented with any architecture designed for passing data and/or control information between processors (such as microprocessors, communications and network processors, etc.), system memory, peripheral devices, and any other hardware components within a computer system. For example, the communications fabric can be implemented, at least in part, with one or more buses.

Medical imaging device 104 is a contrast medium based medical imaging device (such as an MRI device or a CT device) equipped with computer processing and data storage capabilities, including similar components to absorption phase assessment computer 200, in addition to specialized hardware to record contrast medium based medical images and/or scans.

Reference image client 106 is a client computer system including data elements corresponding to a set of reference images of contrast medium based medical images.

Facility management computer 108 is a client computer system operated by management of a facility administering medical imaging diagnostics using medical imaging device 104.

Memory 208 and persistent storage 210 are computer-readable storage media. In general, memory 208 can include any suitable volatile or non-volatile computer-readable storage media. It is further noted that, now and/or in the near future: (i) external device(s) 214 may be able to supply, some or all, memory for subsystem 102; and/or (ii) devices external to subsystem 102 may be able to provide memory for subsystem 102. Both memory 208 and persistent storage 210: (i) store data in a manner that is less transient than a signal in transit; and (ii) store data on a tangible medium (such as magnetic or optical domains). In this embodiment, memory 208 is volatile storage, while persistent storage 210 provides nonvolatile storage. The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communications unit 202 provides for communications with other data processing systems or devices external to subsystem 102. In these examples, communications unit 202 includes one or more network interface cards. Communications unit 202 may provide communications through the use of either or both physical and wireless communications links. Any software modules discussed herein may be downloaded to a persistent storage device (such as persistent storage 210) through a communications unit (such as communications unit 202).

I/O interface set 206 allows for input and output of data with other devices that may be connected locally in data communication with server computer 200. For example, I/O interface set 206 provides a connection to external device(s) 214. External device(s) 214 will typically include devices such as a keyboard, keypad, a touch screen, and/or some other suitable input device. External device(s) 214 can also include portable computer-readable storage media such as, for example, thumb drives, portable optical or magnetic disks, and memory cards. Software and data used to practice embodiments of the present invention, for example, program 300, can be stored on such portable computer-readable storage media. I/O interface set 206 also connects in data communication with display 212. Display 212 is a display device that provides a mechanism to display data to a user and may be, for example, a computer monitor or a smart phone display screen.

In this embodiment, program 300 is stored in persistent storage 210 for access and/or execution by one or more computer processors of processor set 204, usually through one or more memories of memory 208. It will be understood by those of skill in the art that program 300 may be stored in a more highly distributed manner during its run time and/or when it is not running. Program 300 may include both machine readable and performable instructions and/or substantive data (that is, the type of data stored in a database). In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer-readable storage media that is capable of storing program instructions or digital information.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

II. Example Embodiment

Figure 2:
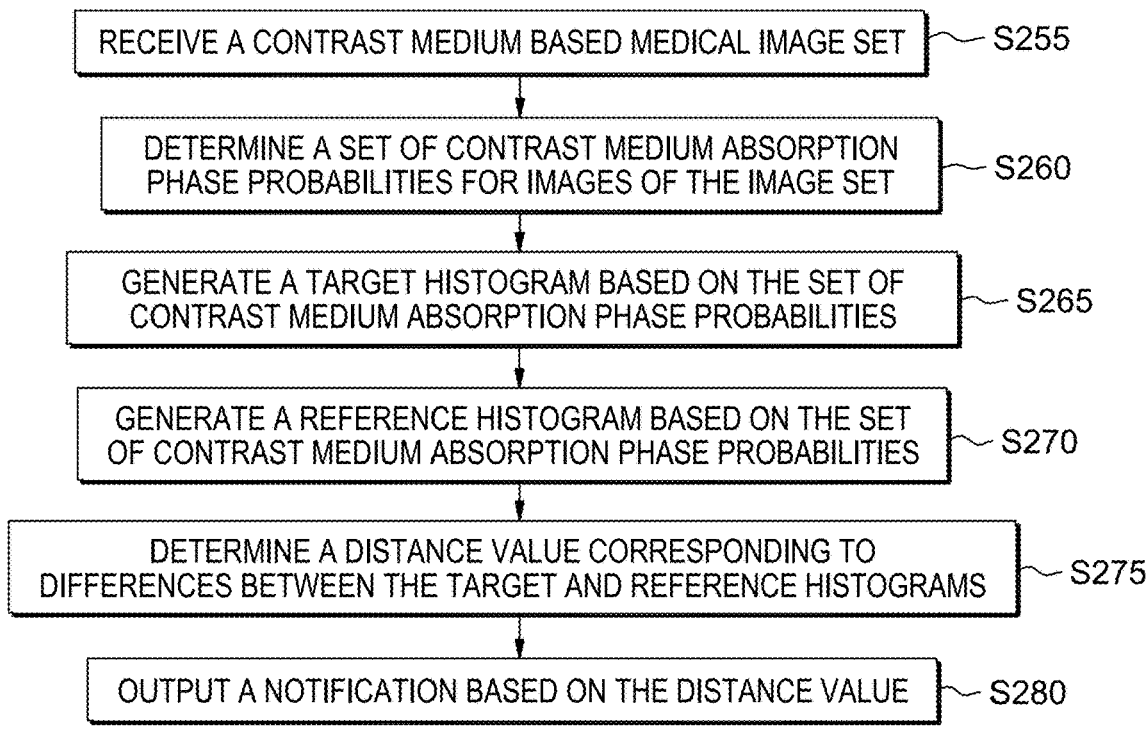
FIG. 2 is a flowchart showing a first embodiment method performed, at least in part, by the first embodiment system.
Figure 3:
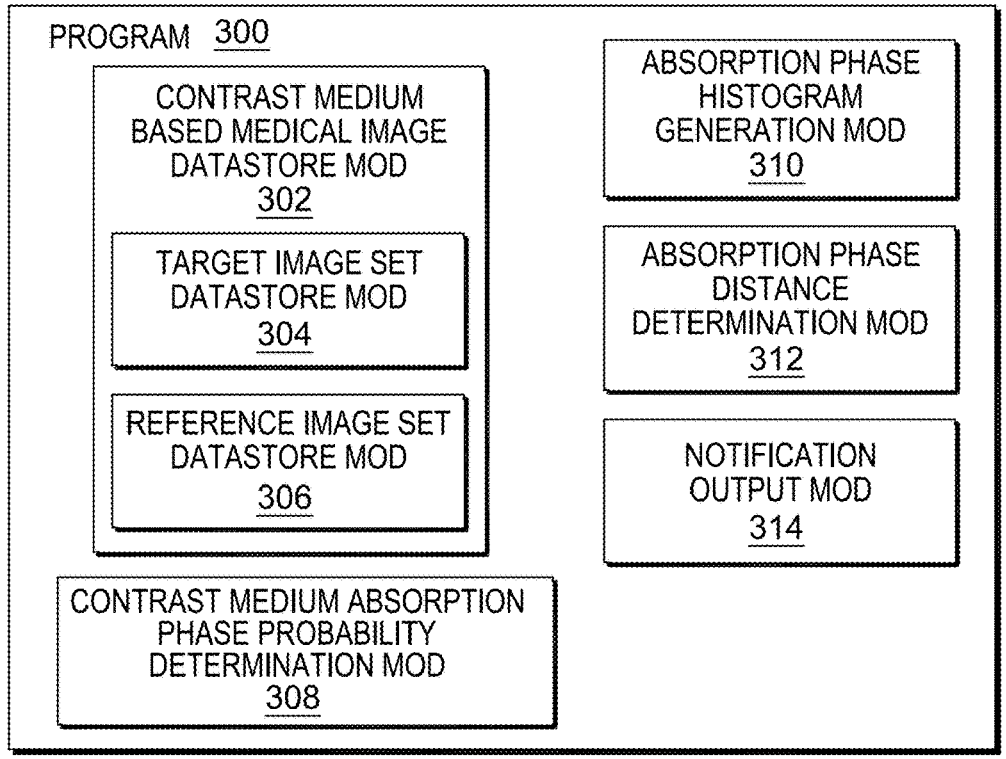
FIG. 3 is a block diagram showing a machine logic (for example, software) portion of the first embodiment system.
Figure 4A:
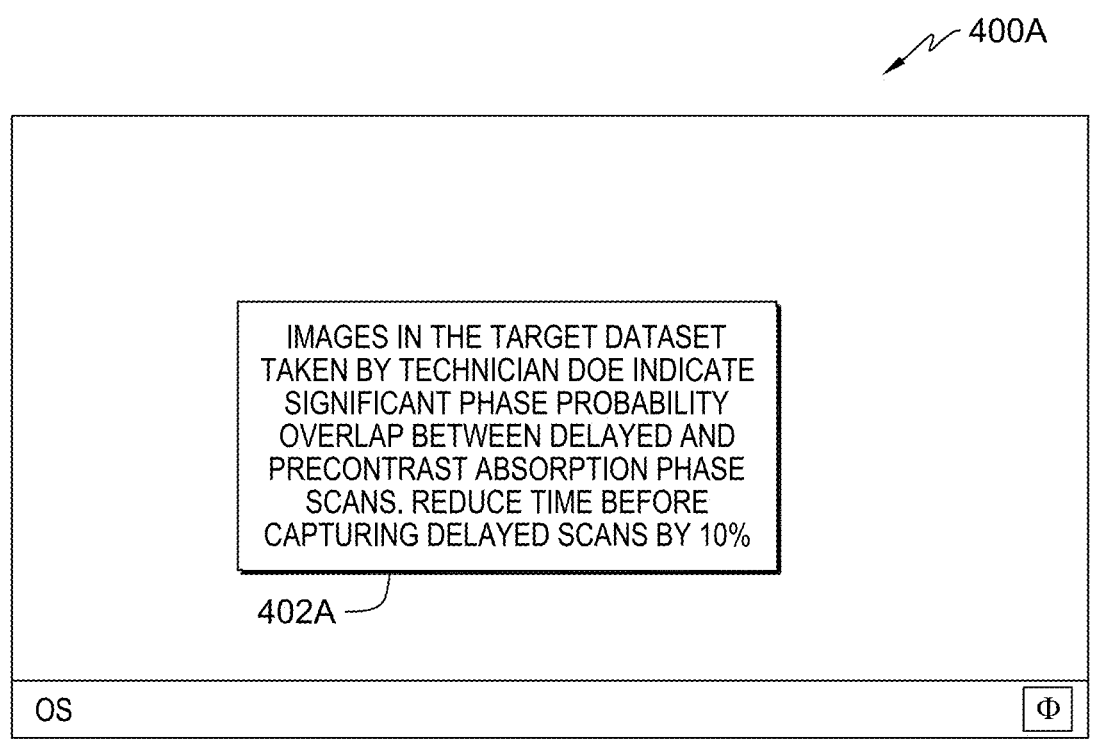
FIG. 4A is a first screenshot view generated by the first embodiment system.
Figure 4B:
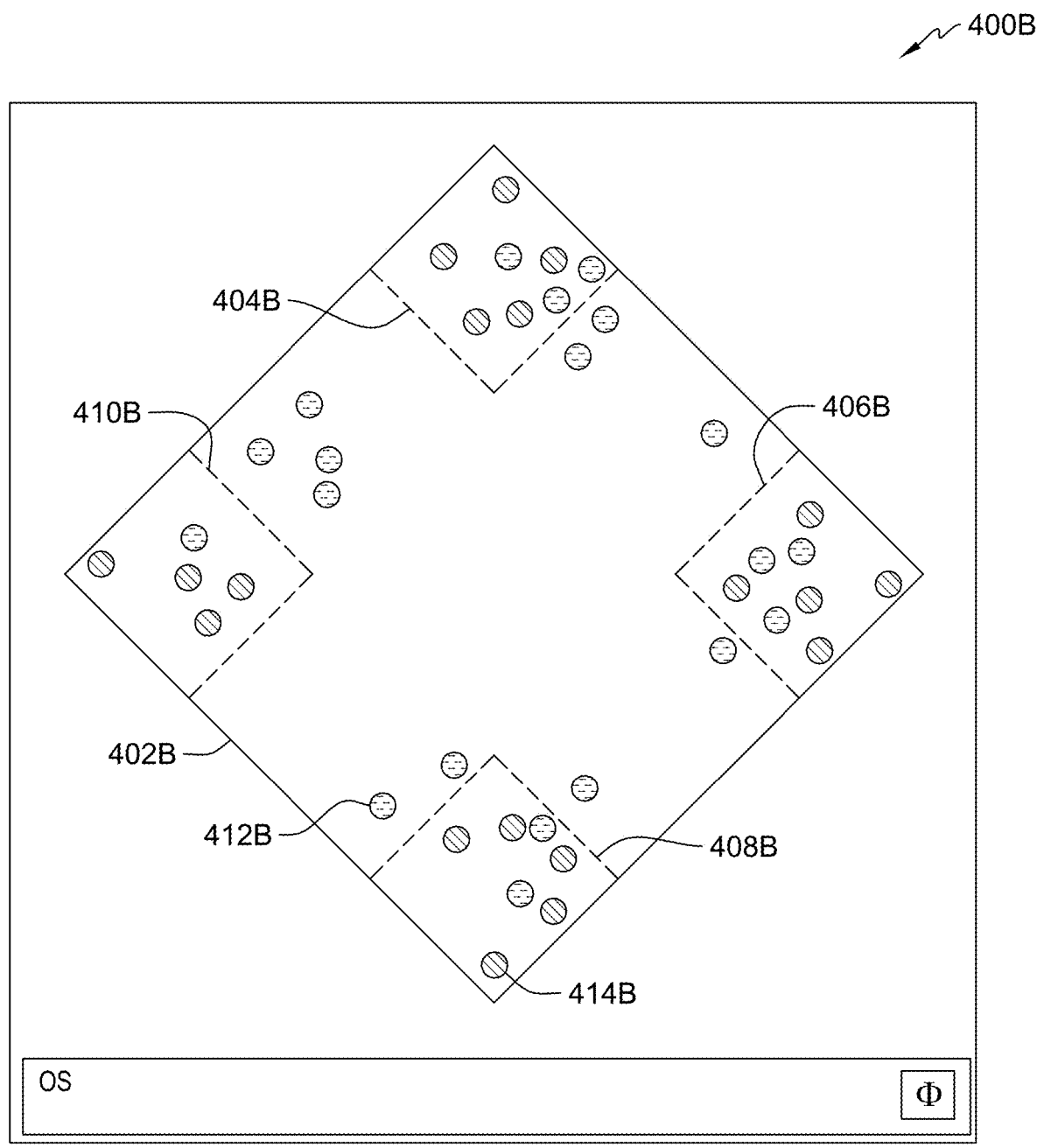
FIG. 4B is a second screenshot view generated by the first embodiment system.

As shown in FIG. 1, networked computers system 100 is an environment in which an example method according to the present invention can be performed. As shown in FIG. 2, flowchart 250 shows an example method according to the present invention. As shown in FIG. 3, program 300 performs or control performance of at least some of the method operations of flowchart 250. This method and associated software will now be discussed, over the course of the following paragraphs, with extensive reference to the blocks of FIGS. 1, 2, 3, 4A and 4B.

Processing begins at operation S255, where contrast medium based medical image data store module ("mod") 302 receives a contrast medium based medical image set. In this simplified embodiment, contrast medium based medical image set includes 40 contrast medium based medical images. A contrast medium based medical image describes any kind of medical image taken using contrast medium to amplify contrast of internal body structures, such as CT and MRI scans. In this simplified embodiment, the 40 contrast medium based medical images include two groups of images: (i) a first subset of twenty images corresponding to a target image set, received over network 114 of FIG. 1 from medical imaging device 104, which is stored in target image set datastore mod 304; and (ii) a second subset of twenty images corresponding to a reference image set, received over network 114 from reference image client 106, which is stored in reference image set datastore mod 306. Various images in each subset correspond to the following four contrast medium absorption phases (CMAPs): (i) precontrast (or PRE, as described below); (ii) arterial (or ART, as described below); (iii) venous (or VEN, as described below); and (iv) delayed (or DEL, as described below). In this simplified embodiment, the reference image set corresponds to CT image scans that are optimal representative example images of the four CMAPs, illustrating clear differences between images corresponding to each CMAP.

In general, certain types of tissues (e.g., a tumor) appear different based on the amount of time that has elapsed after a contrast medium has been administered to a patient. Other factors (e.g., a metabolic rate or heart rate of a patient) may affect how long each phase of the contrast may last. In certain types of diagnostic studies, an example protocol includes four phases (time periods) of the contrast medium. A first phase of the contrast may be referred to as the precontrast phase (PRE) where contrast has not yet been administered. Therefore, in this first PRE phase, the images correspond to a normal volumetric CT scan (i.e., without the use of a contrast medium). A second phase of the contrast may be referred to as the arterial phase (ART). In this second phase, images are acquired soon after administration of contrast medium. In this second phase, early enhancement of an abnormality may be seen if the abnormality has arterial circulation. A third phase of the contrast may be referred to as the portal venous phase (VEN), and this phase corresponds to a state when the contrast reaches portal circulation and is being drained from a target area through the hepatic veins. The portal circulation is a major source of blood supply during this third phase of the contrast. A fourth phase of the contrast may be referred to as the delayed scan phase (DEL), and during this phase a retention of contrast material in, for example, lesions and parenchyma may be seen. It should be appreciated that the present example applies to CECT scans having any suitable number of CPs. For example, other CPs may include early-arterial and nephrogenic CPs.

In some alternative embodiments, other CMAPs are used based on the need of the diagnostic imaging performed. Alternatively, in some embodiments other types of contrast medium based medical images are received (for example, MRI scans). In some other alternative embodiments, contrast medium based medical image data store mod 302 performs population selection, filtering images from the contrast medium based medical image set based on one or more criteria such as: (i) type/vendor of contrast medium injectors; (ii) acquisition devices (make and model of CT devices, MRI devices, etc.); (iii) technologist performing the acquisition; (iv) radiologist; (v) patient age; (vi) sub-facility within a multi-facility organization; (vii) a specified time period (such as those taken within a specified day, week, month, year, etc.); or automatically selecting outlier populations based on subsequent analysis described below. In some further alternative embodiments, images are selected for inclusion in target image set based on a pattern of timing of acquisition for the images corresponding to different contrast medium absorption phases of a given patient, where there are multiple images for a given patient, and the acquisition of each image of the given patient directed towards imaging a different contrast medium absorption phase. Timings between the acquisition of each image is used to determine if the image (or images for the patient) are included in the target set. Images, or areas of an image, exist in a plurality of forms and include: (i) one dimensional images, such as a line with a single pixel of width; (ii) two dimensional, such as rectangular (defined by an X and a Y dimension) or hemispherical; (iii) three dimensional, such as a three dimensional model; (iv) still images (comprising an individual image); and/or (v) videos, or sequences of images displayed in a sequence to illustrate change or motion over time.

Processing proceeds to operation S260, where contrast medium absorption probability determination mod 308 determines a set of contrast medium absorption phase probabilities for images of the image set. In this simplified embodiment, contrast medium absorption probability determination mod 308 determines sets of contrast medium absorption phase probabilities for the images in the target image set data store mod 304 separately from the images in the reference image set data store mod 306. In this simplified embodiment, a set of contrast medium absorption probabilities includes numeric values ranging between 0 and 1 corresponding to a percentage probability that a given image corresponds to one of the CMAPs, with each set including a numeric value for each CMAP. For example, in this simplified embodiment, a given set of contrast medium absorption phase probabilities includes four numeric values, or one for each CMAP discussed above in the simplified embodiment: (i) PRE; (ii) ART; (iii) VEN; and (iv) DEL. The values for the given set might look like: (i) 0.02; (ii) 0.65; (iii) 0.30; and (iv) 0.03. An optimally administered exam would result in an image with a set of contrast medium absorption phase probabilities with one value approaching 1.0 and three values approaching 0, suggestive of a clear and distinct image corresponding to a specific contrast medium absorption phase instead of possibly corresponding to two or more contrast medium absorption phases. Sub-optimally administered exams may have two or more absorption phase probabilities with significant non-zero values indicating a high probability that the corresponding image appears to belong to two or more CMAPs.

For the example in this simplified embodiment, forty sets of contrast medium absorption phase probabilities are determined, with twenty sets of contrast medium absorption phase probabilities corresponding to the images in the target image set data store mod 304 and the other twenty sets of contrast medium absorption phase probabilities corresponding to the images in the reference image set data store mod 306. Each set of contrast medium absorption phase probabilities includes numerical probability values corresponding to probabilities that the image associated with the set of contrast medium absorption phase probabilities corresponds to each of the four CMAPs discussed above.

To determine a probability for a given image to correspond to a CMAP, contrast medium absorption probability determination mod 308 utilizes a trained machine learning model that is built using a reference corpus of contrast medium based medical images labeled with contrast medium absorption phases, which is further refined when supplied with subsequent contrast medium based medical images for classification. This trained machine learning model outputs confidence values, or probability values, that a target image corresponds to the different CMAPs. As images in the target image set data store mod 304 and the reference image set data store mod 306 are supplied to the trained machine learning model of contrast medium absorption probability determination mod 308, four numerical values are outputted by mod 308 corresponding to the four numerical values of the sets of contrast medium absorption phase probabilities.

In some alternative embodiments, the contrast medium absorption phase probabilities are generated from a regression model based on the histograms. In some further alternative embodiments, the regression model is a deep learning model, built using neural networks using the images, such as the images in the contrast medium based medical image set, to output predictions comprising probabilities of which contrast medium absorption phase each image corresponds to. In some other alternative embodiments, the histograms are used to generate a probability density function, where one or more statistical metrics can be derived from concerning the histograms, with the statistical metrics including: (i) mean, (ii) standard deviation, (iii) variance, (iv) skewness, (v) entropy, and (vi) distribution.

Processing proceeds to operation S265, where absorption phase histogram generation mod 310 generates a target histogram based on the set of contrast medium absorption phase probabilities. In this simplified embodiment, a four-dimensional histogram is generated corresponding to the sets of contrast medium absorption phase probabilities associated with the images in target image set datastore mod 304. For each given image in target image set datastore mod 304, the corresponding set of contrast medium absorption phase probabilities is used to plot the position of the given image along the dimensions of the histogram, with one dimension for each CMAP. The resulting target histogram illustrates the distribution of contrast medium absorption phase probabilities for the images in target image set datastore mod 304. In some alternative embodiments, instead of a histogram another data illustration is used, such as a heatmap.

Processing proceeds to operation S270, where absorption phase histogram generation mod 310 generates a reference histogram based on the set of contrast medium absorption phase probabilities. In this simplified embodiment, a four-dimensional histogram is generated corresponding to the sets of contrast medium absorption phase probabilities associated with the images in reference image set datastore mod 306. For each given image in reference image set datastore mod 306, the corresponding set of contrast medium absorption phase probabilities is used to plot the position of the given image along the dimensions of the histogram, with one dimension for each CMAP. The resulting reference histogram illustrates the distribution of contrast medium absorption phase probabilities for the images in reference image set datastore mod 306. In some alternative embodiments, instead of a histogram another data illustration is used, such as a heatmap.

Processing proceeds to operation S275, where absorption phase distance determination mod 312 determines a distance value corresponding to differences between the target and reference histograms. In this simplified embodiment, the term "distance value" is used to represent a matching score in reference to comparisons between two histograms. In this simplified embodiment, the reference histogram is used as a benchmark to define a threshold for evaluating the target histogram, thereby distance from the threshold amounts to distance from the reference histogram. For example, if the images plotted in the reference histogram illustrate that the average image in reference image set datastore mod 306 has a set of contrast medium absorption phase probability values indicative of a 75% to 90% probability of belonging to one of the CMAPs (with equal distribution across the four CMAPs, such as five images with a contrast medium absorption probability of 75% to 90% of belonging to the PRE phase, five corresponding to the ART phase, etc.), while other probability values in the set do not exceed 20%, the threshold might be set to indicate that the images in the target image set datastore mod 304 should correspond to similar probability values. That is, the set of contrast medium absorption phase probability values of the images in target image set datastore mod 304 meet the threshold when indicative of a 75% to 90% probability of belonging to one of the CMAPs, where other probability values in the set do not exceed 20%.

In this simplified embodiment, the distance value comprises four sub-values that are measured as the difference between the threshold(s) defined by the reference histogram and distance values between images in the target histogram from their CMAP with the highest contrast medium absorption phase probability (for example, if the image has a 51% probability of corresponding to a PRE phase, then the distance value for that image is measured as 49%), broken down into buckets for each of the four CMAPs comprising the average of the distance values of the images from their most probable CMAP. For example, if there are 5 images in the target histogram with sets of contrast medium absorption phase probabilities indicative of a greater than 51% probability of corresponding to a VEN phase, then their distance (in probability) from 100% is averaged, and then compared against the threshold defined by the reference image histogram.

In some alternative embodiments, the threshold defined by the reference image histogram comprises four sub-thresholds, separately derived for each CMAP to account for expected differences in precision for different CMAPs. For example, where images acquired for the PRE CMAP are typically more precise than ART or VEN, such as if the images in the reference image set datastore mod 306 corresponding to the PRE CMAP include sets of contrast medium absorption phase probabilities indicating a 95% or greater probability of belonging to the PRE CMAP while the images in the reference image set datastore mod 306 corresponding to the ART CMAP include sets of contrast medium absorption phase probabilities averaging a 85% probability of belonging to the ART CMAP. This alternative provides bespoke thresholds for each CMAP when evaluating the target image histogram.

Processing proceeds to operation S280, where notification output mod 314 outputs a notification based on the distance value. In this simplified embodiment, the notification includes two different notifications: (i) a first notification component, shown in screenshot 400A of FIG. 4A, includes a text-based notification shown in window 402A; and (ii) a second notification component, shown in screenshot 400B of FIG. 4B, includes phase probability diagram 402B. Phase probability diagram 402B further includes: (i) PRE CMAP probability threshold 404B; (ii) ART CMAP probability threshold 406B; (iii) VEN CMAP probability threshold 408B; (iv) DEL CMAP probability threshold 410B; (v) target image set image 412B; and (vi) reference image set image 414B. The notification, including the first notification component and the second notification component, is outputted over network 114 of FIG. 1 to facility management computer 108, and displayed on a display (such as display 212). In some alternative embodiments, only one of the above notifications is outputted (either the text based notification or the phase probability diagram). In other alternative embodiments, a different type of notification is outputted. In yet further alternative embodiments, some combination of the above notifications are outputted.

III. Further Comments and/or Embodiments

Some embodiments of the present invention recognize the following facts, potential problems and/or potential areas for improvement with respect to the current state of the art: (i) some medical imaging modalities like computerized tomography (CT) and magnetic resonance (MR) require the injection of a contrast medium before imaging the patient; (ii) this is mainly done to better assess the presence of pathology and/or to characterize it; (iii) several acquisitions may be performed during the time contrast is distributed in the body to achieve those tasks; (iv) during that time several images are acquired corresponding to different "phase" of the contrast; (v) one variable that directly assess the outcome of the exam is how optimal from a timing standpoint those acquisitions are (i.e. is the acquisition performed as the right level of contrast uptake); (vi) depending on the exam, the acquisitions are normalized for a given task; (vii) for instance, for liver imaging, between one and five phases may be acquired for a given patient; (viii) ideally, each of those phases should be acquired when the contrast medium uptake reaches a specific level; (ix) because of various sources of variability some of those images can be acquired too early or too late; (x) this can translate into huge variability in image quality; and (xi) detection of suboptimal phase timing may not be obvious especially in situations when the actual images do not display any obvious artifacts Some embodiments of the present invention may include one, or more, of the following operations, features, characteristics and/or advantages: (i) a technique to assess the quality of phase imaging in a patient population (e.g. a clinical site, performed by a given team, or by a particular technologist or camera, etc.); (ii) it can prompt that correctable actions are required (such as identification of training needs for clinical personnel and/or assessment of trends); (iii) automatic analysis of phase images; (iv) the technique defines a metric and computes this metric for a given exam; (v) this creates scores indicating how far the phases are from an ideal phase timing for a given scan; (vi) taking into account distributions of those scores, the technique can also report either general performance of the institution, department, scanner, technologist, etc.; (vii) population selection includes fixed criteria such as: (a) type/vendor of injectors, (b) acquisition devices (make and model), (c) technologist, (d) radiologist, (e) patient age; (f), sub-facility in cases of multi-center organization, and (g) time period; (viii) population selection may also include automatic extraction of outlier populations; (ix) a classification stage includes: (a) statistical analysis/distance on histogram, (b) extraction of features (e.g. entropy, variance, overlap on mods) with threshold to make a decision, and (c) classifier (e.g. DL model) that associate good/bad profile to the input histogram(s); (x) the classification stage may also use reference histogram/comparison data, for instance: (a) population from another site, (b) pre-computed standard population, (c) synthetic histogram built and tailored for a given site (what it expected by customer at this site), and (d) histogram from the site without its outliers; (xi) additional outcomes may include: (a) detect trending of injection quality degradation or improvement, (b) automatic/manual alert generation, (c) visual layout to give insight on what need to be improved, (d) prediction of acquisition/injection parameters from the analysis of a patient acquisition; and (xii) derive population based measures to exhibit discrepancies between populations in order to detect anomalies that occurs in time in a fully automated manner.

Some embodiments of the present invention may include one, or more, of the following operations, features, characteristics and/or advantages: (i) a technique to analyze one or more medical images acquired using contrast medium; (ii) provide a feedback on the quality of the images based on the state of the contrast; (iii) the medical images can be CT, MR, Xray, mammography or tomography; (iv) the analysis is performed by computing degree/probability to belong to a specific phase of the contrast; (v) this is used to derive how far the acquisition(s) is/are from an ideal set of acquisition; (vi) the acquisitions may be derived from a single exam; (vii) the acquisitions are derived from several exams of one or more patients; (viii) the analysis is performed using a neural network assigning a score to belong to each phase, where the criterion is a measure on the shape on the distribution of those scores; (ix) the measure is entropy, variance or skewness, overlap on distributions of predicted phases; (x) the analysis is reported to raise an alert for low quality of one or several exams; (xi) the trend over time of the quality of a set of exams is reported; (xii) a visual diamond is used to report the quality of a set of exams; and (xiii) where the set of image analyzed are split according to exam type.

Some embodiments of the present invention may include one, or more, of the following operations, features, characteristics and/or advantages: (i) receive all the scans of a clinical site; (ii) compute the type of exam (e.g. select abdominal scans); (iii) compute the probability using a Neural Net for each acquisition to belong to a given phase and build up distributions of those values; (iv) this distribution is analyzed either ad hoc or on a regular basis to determine how far it is from an acceptable distribution (e.g. variance for each phase, entropy of all the phases, etc.); and (v) an alert is sent to a predefined person if deviation is detected Some embodiments of the present invention may include one, or more, of the following operations, features, characteristics and/or advantages: (i) automatically compute the distributions of contrast phases as described above; (ii) a user uses a UI or an API to select a subset of data (can be: (a) all data over a period of time, (b) acquisition involving a given tech/radiologist or scanner, (c) data for a given acquisition technique like single phase CT or multiphase CT, etc.); (iii) compute quality data for the selected set and report it; and (iv) a visual assessment tool with derived metrics and, in some embodiments, thresholds on deviations of the metrics defining acceptable quality.

Some embodiments of the present invention may include one, or more, of the following operations, features, characteristics, advantages and/or significant variations: (i) analysis can be automated; (ii) analysis can be manually triggered; (iii) the set of scans can be anything (e.g. all scans, set that matches some criteria, those done by a given person); (iv) analysis can be done using several measures (e.g. entropy, variance, overlap on mods); (v) an alert can be sent on automatic analysis; (vi) a visual layout can be displayed (such as a diamond diagram as shown in other embodiments described above) to visually assess the quality on a given population; and (vii) an interface (e.g. web page) may be used to report the results.

Figure 5:
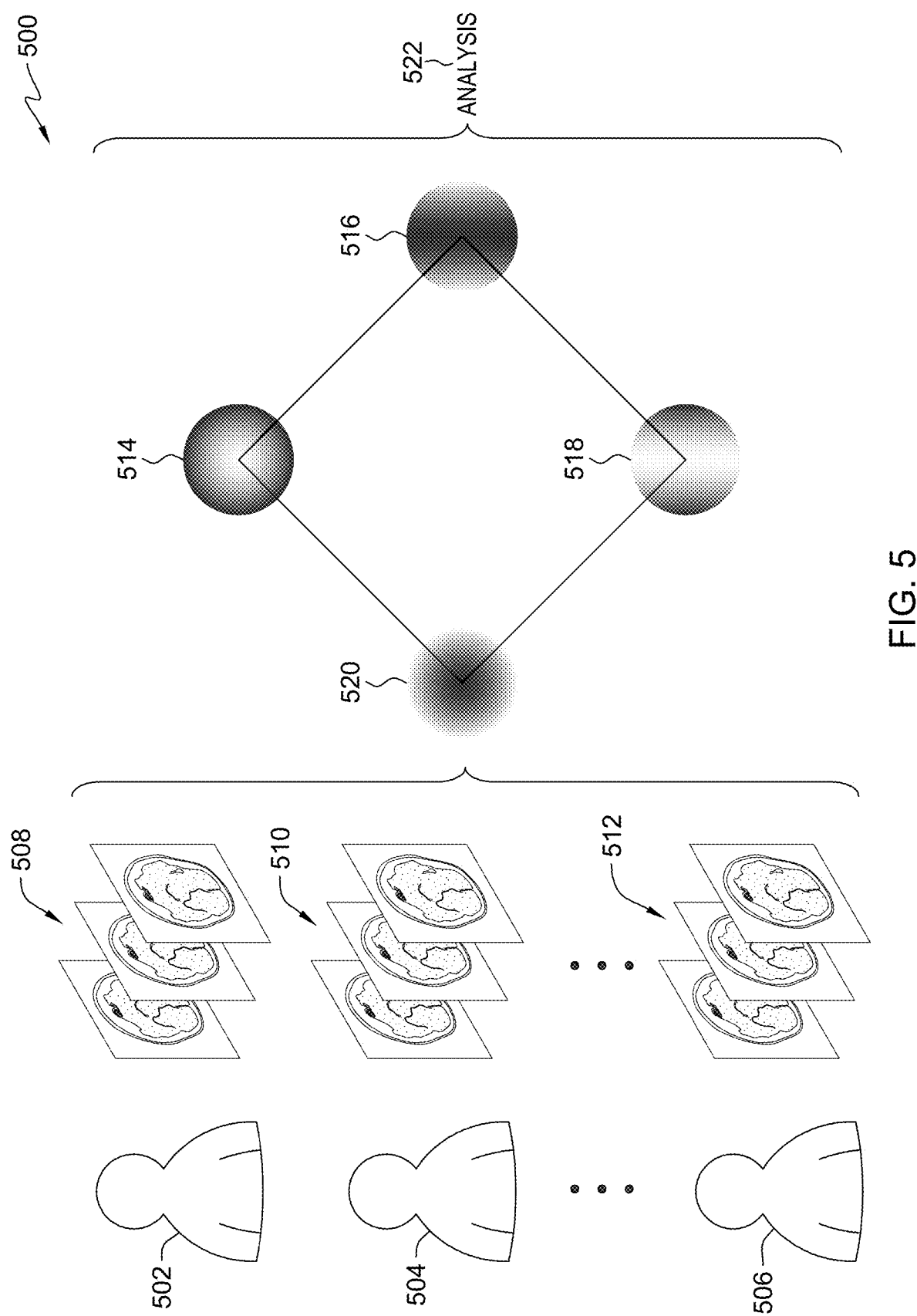
FIG. 5 is a block diagram view illustrative of a second embodiment method.

FIG. 5 shows diagram 500, including: (i) patient 1 502; (ii) patient 2 504; (iii) patient n 506; (iv) patient 1 medical image set 508; (v) patient 2 medical image set 510; (vi) patient n medical image set 512; (vii) precontrast absorption phase 514; (viii) arterial absorption phase 516; (ix) portal/venous absorption phase 518; (x) delayed absorption phase 520; and (xi) analysis module 522. In this embodiment, each patient (such as patient 1 502) includes a corresponding set of medical images (such as patient 1 medical image set 508). The set(s) of medical images includes scans taken using contrast-medium supported medical imaging modes (such as CT scans, or MR scans), with each set including at least one image corresponding to each of the following contrast medium absorption phases: (i) precontrast; (ii) arterial; (iii) venous; and (iv) delayed. For each image, a machine learning component automatically determines a probability for the image to correspond to each contrast medium absorption phase. Analysis module 522 then analyzes the determined probabilities for the entire corpus of images (508, 510 . . . 512) to determine how far the images are "spread" from an ideal distribution across the four contrast medium absorption phase. For example, analysis module 522 will analyze the determined probabilities to determine how commonly medical images from the corpus are determined to be substantially likely to correspond to either precontrast absorption phase 514 or arterial absorption phase 516, which may suggest in one example that insufficient time is being allowed to elapse between capturing scans corresponding to a precontrast absorption phase and an arterial absorption.

Figure 6:
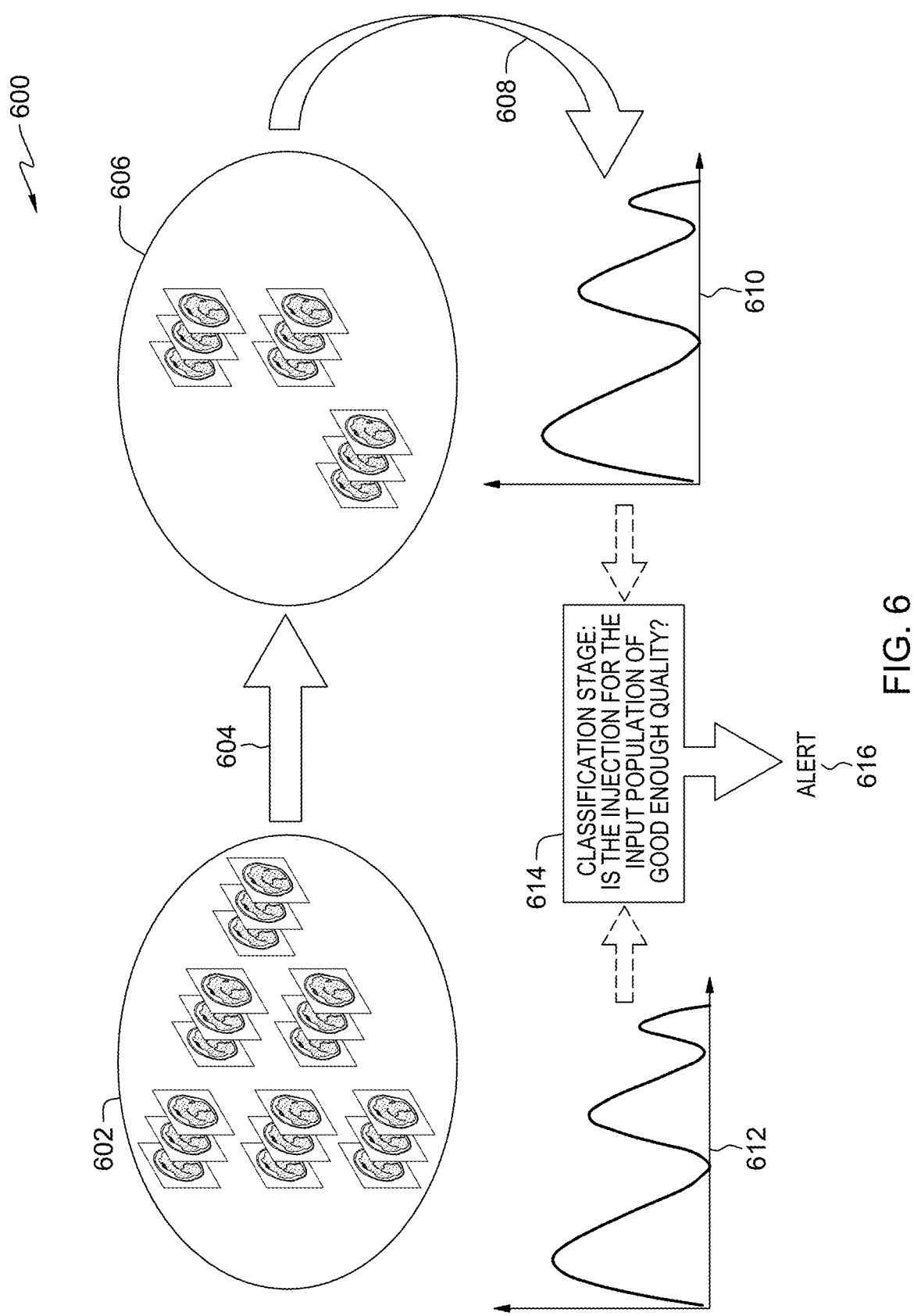
FIG. 6 is a block diagram view illustrative of a third embodiment method.

FIG. 6 shows diagram 600, including: (i) set of medical image scans 602; (ii) medical image scan sub-selection module 604; (iii) medical image scan subset 606; (iv) phase probability calculation module 608; (v) multidimensional histogram 610; (vi) reference population histogram 612; (vii) classification module 614; and (viii) alert module 616. In this embodiment, the set of medical image scans 602 is sourced from a single facility. After receiving the set of medical image scans 602, medical image scan sub-selection module 604 selects a sub-set of cases and their associated scans, resulting in medical image scan subset 606. Next, each image in medical image scan subset 606 is processed through phase probability calculation module 608 to determine probabilities for each image to belong to one of several contrast medium absorption phases, resulting in a multidimensional histogram 610 (with one dimension for each contrast medium absorption phase, or four dimensions in some preferred embodiments) showing the distribution of probabilities. A reference population histogram 612 is then used to by classification module 614 to classify multidimensional histogram 610. Should the classification indicate that the histogram significantly deviates from reference population histogram 612, alert module 616 sends an alert to staff of the single facility if the analyzed set of scans is too bad/too far from the target one.

Figure 7:
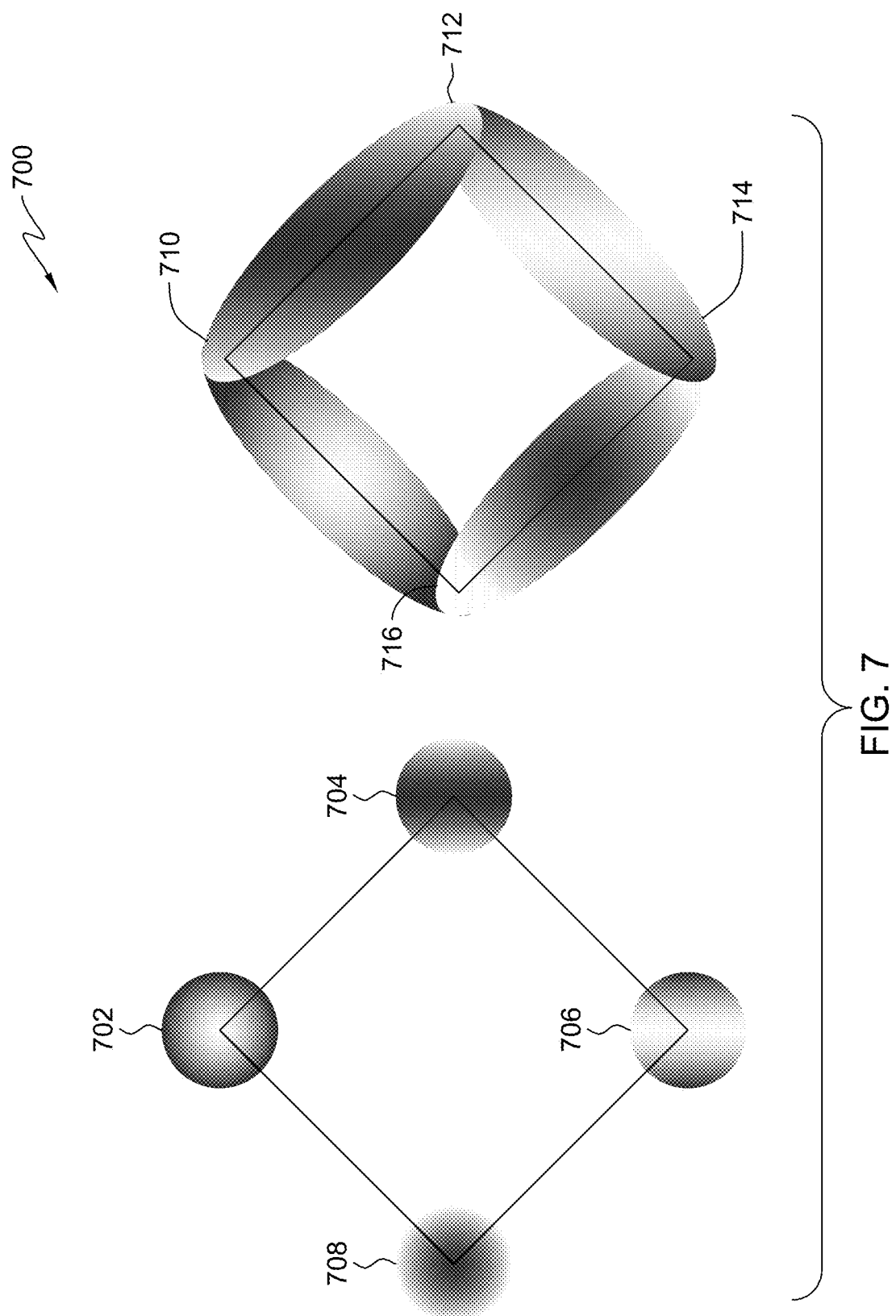
FIG. 7 is a block diagram view illustrative of contrast absorption phase distributions.

FIG. 7 shows diagram 700, including: (i) optimal precontrast phase histogram distribution 702; (ii) optimal arterial phase histogram distribution 704; (iii) optimal portal/venous phase histogram distribution 706; (iv) optimal delayed phase histogram distribution 708; (v) sub-optimal precontrast phase histogram distribution 710; (vi) sub-optimal arterial phase histogram distribution 712; (vii) sub-optimal portal/venous phase histogram distribution 714; and (viii) sub-optimal delayed phase histogram distribution 716. In this embodiment, 702 through 708 show an "ideal" histogram distribution for a set of scans corresponding to four contrast medium absorption phases. Each given scan or image was assigned high probabilities to belong to only one of the four absorption phases, suggesting optimal timing for contrast medium absorption between when each image or scan was acquired. In contrast, 710 through 716 show a "sub-optimal" histogram distribution for a set of scans corresponding to four contrast medium absorption phases. Many scans or images were assigned significant probabilities to belong to two or more contrast medium absorption phases, suggesting potential problems with how the scans or images were acquired (such as too little or too much time between performing imaging after administering contrast medium to a patient or time between scans or images).

Figure 8:
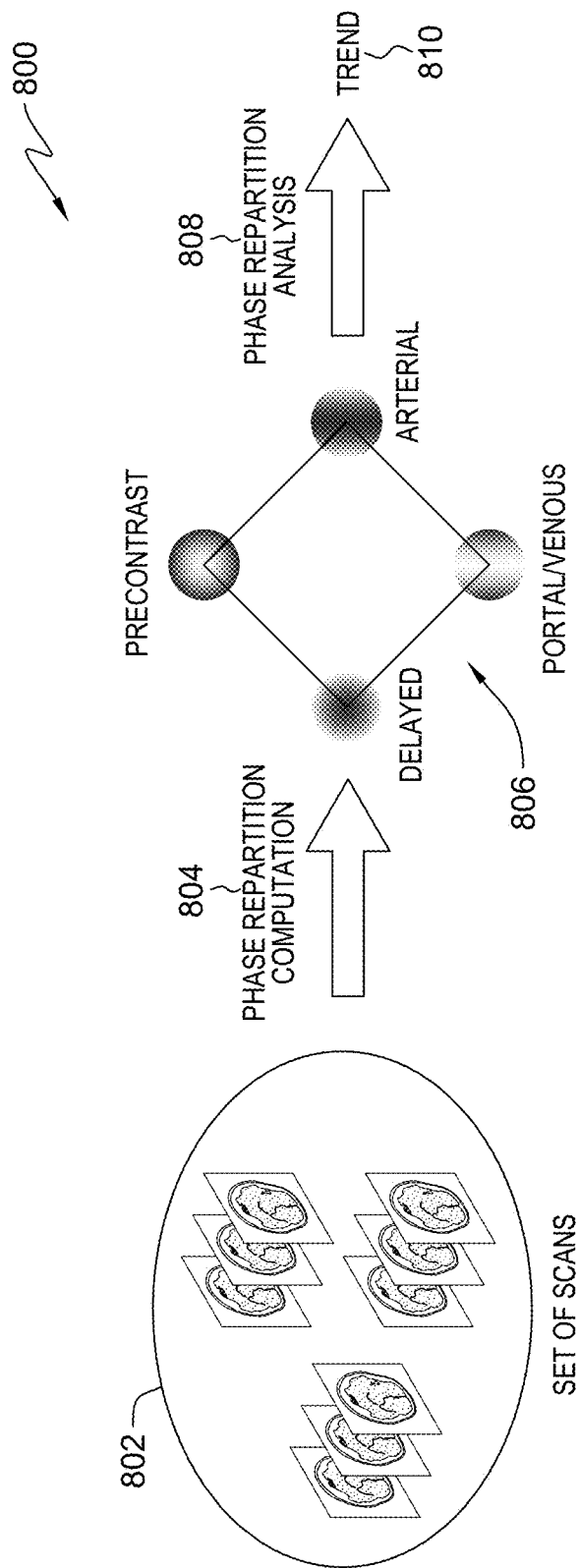
FIG. 8 is a block diagram view illustrative of a fourth embodiment method.

FIG. 8 shows diagram 800, including: (i) set of scans 802; (ii) phase repartition computation module 804; (iii) phase repartitions 806; (iv) phase repartition analysis module 808; and (v) trend determination module 810.

Some embodiments of the present invention may include one, or more, of the following operations, features, characteristics and/or advantages: (i) assessing whether a set of exams/acquisition are far way or not from a reference set of exams; (ii) identifying groups of exams of poorer quality (or far away from a given reference); (iii) assess a posteriori how well exams are performed on a given population; (iv) analyzing population-based features of CT scans; (v) assess the quality of already acquired injected images on a population; (vi) assessing quality of already acquired exams on a given population; (vii) classification of population phase-based features histograms; (viii) assessing the image injection quality of a given population; (ix) sending an alert based on analysis of a population of exams; (x) analysis of contrast injection impact on image exams on a given population; (xi) assesses the quality of exams on a population, which are not necessarily taken on the same device; (xii) finding if injection quality is good or bad on a given population; (xiii) root cause may be the use of the device (acquisition or injection), patient specific characteristics, etc., which goes way beyond how well the system was calibrated; (xiv) additionally work on already acquired data; (xv) analyzing how good was the injection of already acquired exams; (xvi) analysis of already acquired exams; and (xvii) finding population of lower quality injection from existing exams.

According to an aspect of the present invention, there is a method, computer program product and/or system for image based phase contrast quality assessment that performs the following operations (not necessarily in the following order): (i) receiving a plurality of medical images I1, I2, ... In, wherein the medical images are taken of a set of patients forming a set of exams to assess a set of conditions of the patient(s) with a corresponding set of patient demographics after the patient(s) receive a contrast medium; (ii) analyzing the medical images I1, I2, ... In to determine an absorption phase A (A1, A2, ... An) wherein the absorption phase Aj is a representation of absorption phase of the contrast medium in the image Ij; (iii) comparing the absorption phase A (A1, A2, ..., An) to a reference knowledge base including a reference knowledge expected quality to determine a quality assessments QA (QA1, QA2, ... QAn) of the medical images I (I1, I2, ..., In); and (iv) providing a report of the quality assessments QA (QA1, QA2, ..., QAn). In some embodiments, as immediately above, further comprising: (i) analyzing the report of a given set of images Ij to predict if a quality assessment QAj is lower than the reference knowledge expected quality. In some embodiments, as immediately above, further comprising: (i) wherein a selected set of exams in the set of exams is filtered according to one or more criteria [e.g. injectors, acquisition devices, technicians, radiologists, and patient ages.]

IV. Definitions

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein are believed to potentially be new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

In an Including/include/includes: unless otherwise explicitly noted, means "including but not necessarily limited to."

Module/Sub-Module: any set of hardware, firmware and/or software that operatively works to do some kind of function, without regard to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, and application-specific integrated circuit (ASIC) based devices.

Without substantial human intervention: a process that occurs automatically (often by operation of machine logic, such as software) with little or no human input; some examples that involve "no substantial human intervention" include: (i) computer is performing complex processing and a human switches the computer to an alternative power supply due to an outage of grid power so that processing continues uninterrupted; (ii) computer is about to perform resource intensive processing, and human confirms that the resource-intensive processing should indeed be undertaken (in this case, the process of confirmation, considered in isolation, is with substantial human intervention, but the resource intensive processing does not include any substantial human intervention, notwithstanding the simple yes-no style confirmation required to be made by a human); and (iii) using machine logic, a computer has made a weighty decision (for example, a decision to ground all airplanes in anticipation of bad weather), but, before implementing the weighty decision the computer must obtain simple yes-no style confirmation from a human source.

Automatically: without any human intervention.

What is claimed is:

1. A computer-implemented method (CIM) comprising:
receiving a contrast medium based medical image set, including a target image set, where images in the contrast medium based medical image set are created by different areas in a given image being respectively characterized by a plurality of contrast medium absorption phases;
receiving a reference set of contrast medium absorption phase probabilities;
determining, for each image in the target image set, a set of contrast medium absorption phase probabilities;
creating four sub-thresholds corresponding to the reference set, wherein the four subthreshold are named, PRE, ART, VEN and DEL, respectively;
determining one or more precision values to be assigned to the four sub-thresholds associated with an expected differences in precision between PRE, ART, VEN and DEL, wherein at least one or more precision values can be calculated by:
comparing whether the target image set against the reference set of contrast medium absorption phase probabilities has a 95% or greater probability of belonging to one of the four sub-threshold;
assigning the one or more precision values to the four sub-thresholds; and
computing a set of matching scores based on a distance value between value between the sets of contrast medium absorption phase probabilities of the images of the target image set and the reference set of contrast medium absorption phase probabilities and based on the one or more precision values belonging to the four sub-thresholds.

2. The CIM of claim 1, wherein the reference set of contrast medium absorption phase probabilities is determined from a reference image set.

3. The CIM of claim 1, wherein the set matching scores is computed from histograms based on the sets of contrast medium absorption phase probabilities of the target image set and the reference set of contrast medium absorption phase probabilities.

4. The CIM of claim 3, wherein the set of matching scores are based, at least in part, on a regression model that is based, at least in part, on the histograms.

5. The CIM of claim 4, where the regression model is a deep learning model.

6. The CIM of claim 3, wherein:
the set of matching scores is based, at least in part, on at least one statistical metric derived from a probability density function;
the at least one probability density function is based, at least in part, on the histograms; and
the at least one statistical metric is selected from the group comprising: mean, standard deviation, variance, skewness, entropy, and distribution.

7. The CIM of claim 1, further comprising:
selecting images for inclusion in the target image set from a larger set of images based, at least in part, on at least one of the following criteria: (i) a given range of patient age of patients imaged in the images, (ii) a given make of contrast medium injector corresponding to injected contrast media in the images, (iii) a given model of contrast medium injector corresponding to the injected contrast media in the images, (iv) a given make of imaging device that captured the images, (v) a given model of imaging device that captured the images, (vi) a given technician that operated imaging device(s) that captured the images, (vii) time of acquisition within a predetermined period of time, and/or (viii) a pattern of timing of acquisition for the images corresponding to different contrast medium absorption phases of a given patient.

8. The CIM of claim 1, wherein at least one of the set of matching scores is monitored over time to assess changes in quality of contrast medium injection and image acquisition.

9. The CIM of claim 1, further comprising:
comparing the set of matching scores to a predetermined given threshold value.

10. The CIM of claim 9, further comprising:
outputting a notification over a computer network to a computer device based, at least in part, on the comparison of the set of matching scores to the predetermined threshold value.

11. The CIM of claim 10, wherein the notification includes a phase probability diagram illustrating distribution of the set of contrast medium absorption phase probabilities of the target image set relative to the reference set of contrast medium absorption phase probabilities.

12. The CIM of claim 1, wherein the plurality of contrast medium absorption phases includes: (i) a precontrast phase, (ii) an arterial phase, (iii) a venous phase, and (iv) a delayed phase.

13. The CIM of claim 1, wherein the contrast medium based medical image set corresponds to medical images acquired using contrast media administered to patients using at least one of the following imaging modalities: (i) computed tomography, and (ii) magnetic resonance.

14. A computer program product (CPP) comprising:
a machine readable storage device; and
computer code stored on the machine readable storage device, with the computer code including instructions for causing a processor(s) set to perform operations including the following:
receiving a contrast medium based medical image set, including a target image set, where images in the contrast medium based medical image set are created by different areas in a given image being respectively characterized by a plurality of contrast medium absorption phases;
receiving a reference set of contrast medium absorption phase probabilities;
determining, for each image in the target image set, a set of contrast medium absorption phase probabilities;
creating four sub-thresholds corresponding to the reference set, wherein the four subthreshold are named, PRE, ART, VEN and DEL, respectively;
determining one or more precision values to be assigned to the four sub-thresholds associated with an expected differences in precision between PRE, ART, VEN and DEL, wherein at least one or more precision values can be calculated by:
comparing whether the target image set against the reference set of contrast medium absorption phase probabilities has a 95% or greater probability of belonging to one of the four sub-threshold;
assigning the one or more precision values to the four sub-thresholds; and
computing a set of matching scores based on a distance value between value between the sets of contrast medium absorption phase probabilities of the images of the target image set and the reference set of contrast medium absorption phase probabilities and based on the one or more precision values belonging to the four sub-thresholds.

15. The CPP of claim 14, wherein the set matching scores is computed from histograms based on the sets of contrast medium absorption phase probabilities of the target image set and the reference set of contrast medium absorption phase probabilities.

16. The CPP of claim 14, wherein the computer code further includes instructions for causing the processor(s) set to perform the following operations:
comparing the set of matching scores to a predetermined given threshold value;
outputting a notification over a computer network to a computer device based, at least in part, on the comparison of the set of matching scores to the predetermined threshold value.

17. The CPP of claim 14, wherein the plurality of contrast medium absorption phases includes: (i) a precontrast phase, (ii) an arterial phase, (iii) a venous phase, and (iv) a delayed phase.

18. A computer system (CS) comprising:
a processor(s) set;
a machine readable storage device; and
computer code stored on the machine readable storage device, with the computer code including instructions for causing the processor(s) set to perform operations including the following:
receiving a contrast medium based medical image set, including a target image set, where images in the contrast medium based medical image set are created by different areas in a given image being respectively characterized by a plurality of contrast medium absorption phases;
receiving a reference set of contrast medium absorption phase probabilities;
determining, for each image in the target image set, a set of contrast medium absorption phase probabilities;

creating four sub-thresholds corresponding to the reference set, wherein the four subthreshold are named, PRE, ART, VEN and DEL, respectively;

determining one or more precision values to be assigned to the four sub-thresholds associated with an expected differences in precision between PRE, ART, VEN and DEL, wherein at least one or more precision values can be calculated by:

comparing whether the target image set against the reference set of contrast medium absorption phase probabilities has a 95% or greater probability of belonging to one of the four sub-threshold;

assigning the one or more precision values to the four sub-thresholds; and computing a set of matching scores based on a distance value between value between the sets of contrast medium absorption phase probabilities of the images of the target image set and the reference set of contrast medium absorption phase probabilities and based on the one or more precision values belonging to the four sub-thresholds.

19. The CS of claim 18, wherein the set matching scores is computed from histograms based on the sets of contrast medium absorption phase probabilities of the target image set and the reference set of contrast medium absorption phase probabilities.

20. The CS of claim 18, wherein the plurality of contrast medium absorption phases includes: (i) a precontrast phase, (ii) an arterial phase, (iii) a venous phase, and (iv) a delayed phase.

* * * * *